(12) United States Patent
Kim (10) Patent No.: US 7,879,765 B2
(45) Date of Patent: Feb. 1, 2011

(54) METHOD AND APPARATUS FOR DETECTING BIO-CHIP BY USING PHASE-CHANGE

(75) Inventor: Soo-Kyung Kim, Seoul (KR)

(73) Assignee: Nanostorage Co., Ltd., Seoul (KR)

( * ) Notice: Subject to any disclaimer, the term of this patent is extended or adjusted under 35 U.S.C. 154(b) by 110 days.

(21) Appl. No.: 12/443,516

(22) PCT Filed: Sep. 13, 2007

(86) PCT No.: PCT/KR2007/004416

§ 371 (c)(1),
(2), (4) Date: Mar. 30, 2009

(87) PCT Pub. No.: WO2008/035881

PCT Pub. Date: Mar. 27, 2008

(65) Prior Publication Data

US 2010/0016174 A1    Jan. 21, 2010

(30) Foreign Application Priority Data

Sep. 21, 2006   (KR) .................. 10-2006-0091648
Jan. 30, 2007   (KR) .................. 10-2007-0009624

(51) Int. Cl.
*C40B 30/04* (2006.01)
*C40B 60/12* (2006.01)
*G01N 21/00* (2006.01)

(52) U.S. Cl. .............. 506/9; 422/57; 506/39; 977/958

(58) Field of Classification Search .......... 422/57; 506/9, 39; 977/902, 932, 953, 957, 958
See application file for complete search history.

(56) References Cited

U.S. PATENT DOCUMENTS

2003/0030817 A1    2/2003  Lee et al.

FOREIGN PATENT DOCUMENTS

| KR | 1020050008148 A | 1/2005 |
| KR | 1020060020229 A | 3/2006 |
| KR | 1020060083112 A | 7/2006 |
| WO | 03/098216 A1 | 11/2003 |

OTHER PUBLICATIONS

Y.-F. Chau et al., Deformation and Plasmon Effects of Deformed AgOx-Type Super-Resolution Near-Field Structure, 45 Jpn. J. Appl. Phys. 7228-7230 (2006).*
T. Arai et al., Toward Biological Diagnosis System Based on Digital Versatile Disc Technology, 46 Jpn. J. Appl. Phys. 4003-4006 (2007).*
International Search Report; mailed Dec. 28, 2007; PCT/KR2007/004416.

* cited by examiner

*Primary Examiner*—Glenn Caldarola
*Assistant Examiner*—Randy Boyer
(74) *Attorney, Agent, or Firm*—Ladas & Parry LLP

(57) ABSTRACT

A biochip and a biochip scanning method and apparatus using phase changes are provided, wherein a laser beam is radiated to a biochip having immobilized probes placed thereon to cause a phase change in a phase change layer located under the biochip and the reflectance on the phase change layer according to the phase change is detected to allow reproduction or recording of bio information on the biochip. A phase change biochip and a phase change detection method using phase changes based on resistance detection are also provided, wherein the resistance between two electrodes connected respectively to both ends of a phase change layer including a bio spot where a phase change occurs is measured so that it is possible to easily detect phase changes in the biochip based on changes in the resistance.

11 Claims, 5 Drawing Sheets

METHOD AND APPARATUS FOR DETECTING BIO-CHIP BY USING PHASE-CHANGE

TECHNICAL FIELD

The present invention is to implement a detection technology for phase-change micro-array semiconductor biochips. This technology relates to a bio information detection technology and system which can perform high-speed detection with a high detection reliability and a high reaction stability using a non-fluorescence detection method employing nanoparticles, instead of using a currently available fluorescence detection-based biochip scanner.

More particularly, the invention relates to a biochip detection system that removes factors causing the increase in the price and the instability of the fluorescence detection type and adopts a phase change-based optical disc recording/reproduction technology that has a high technical completeness and reliability proved using nanobeads or nanoparticles. This system uses a method of detecting phase changes of a recording layer on a substrate of the biochip and changes in an organic dye layer based on presence or absence of nanoparticles using a DVD optical pickup mechanism. This is a breakthrough technology that replaces the conventional bio information detection method based on fluorescence causing problems with a non-fluorescence detection method to achieve an improvement in the performance.

BACKGROUND ART

The present invention relates to a biochip scanning method and apparatus using phase changes and more particularly to a biochip detection method and apparatus using phase changes based on reflectance detection, wherein a laser beam is radiated to a biochip having immobilized probes placed thereon to cause a phase change in a phase change layer located under the biochip and the reflectance on the phase change layer according to the phase change is detected to allow reproduction or recording of bio information on the biochip.

The following is a basic principle of the detection method using phase changes according to the invention. $Ge_2Sb_2Te_5$ (GST) is a phase change optical recording material that is widely used as a recording medium for Digital Versatile Disks (DVDs), Phase change Random Access Memory (PRAM), or the like. The GST has the characteristics of reversible phase changes between amorphous and crystalline states. Information is optically written or erased using the reversible phase change characteristics of the GST, thereby obtaining information that is required for the invention.

The invention also relates to a biochip detection method using phase changes and more particularly to a biochip detection method using phase changes based on resistance detection, wherein the resistance between two electrodes connected respectively to both ends of a phase change layer including a bio spot where a phase change occurs is measured so that it is possible to easily detect phase changes in the biochip.

A conventional biochip is constructed by attaching biomolecule probes such as DNA or protein to be analyzed to a substrate. This makes it possible to analyze gene expression patterns, gene defects, protein distribution, and reaction patterns in a sample. The biochip can be classified according to the type of attachment of probes into a microarray chip with probes being attached to a solid substrate and a lab-on-a-chip with probes being attached to a micro-channel. That is, the biochip includes a substrate on which biological materials such as nucleic acid is fixed. A well known biochip is a DNA chip. The DNA chip includes a substrate on which DNAs are fixed. A protein chip includes a substrate on which proteins are fixed.

A system for detecting whether or not target molecules have been bound to immobilized probes on a substrate is required to determine whether or not target molecules that can be bound to probes are present on a sample of the biochip.

A general method to read information from the biochip is to detect the intensity of light emitted from fluorescent materials included in probe molecules. A typical method is laser-induced fluorescence detection. In this method, a laser is used as an excitation light source of a wavelength to be absorbed by the fluorescent material. The laser radiates a laser beam to bring the fluorescent material into an excited state. The system detects the intensity of fluorescent light that the fluorescent material emits when it returns to the ground state. The strength of binding of immobilized probes to target probes (i.e., bio information) can be determined from the intensity of the fluorescent light. Quantitative analysis can be performed by attaching fluorescent materials to a DNA or protein sample in the above manner.

The most frequently used apparatus for detecting fluorescent light using the laser-induced fluorescence detection method is a confocal laser scanning system. The confocal laser scanning system uses laser as a light source and receives a fluorescent signal emitted from a sample using a photomultiplier tube, which is a special detector, and converts it into a digital image using an A/D converter.

The following is an example of the DNA chip detection method. A DNA sample is mostly labeled with a fluorescent dye and is then reacted with probes on a DNA chip for gene analysis and a fluorescent material remaining on the surface of the chip is detected using a confocal microscope or a CCD camera (see U.S. Pat. No. 6,141,096).

However, it is difficult to design a small-size system according to this optical detection method. This method also does not support digital outputs. Thus, many studies have been done to develop a new detection method that provides detection results using electrical signals.

Many research institutes including the Clinical Micro Sensor have studied a method to electrochemically detect DNA hybridization using metal compounds which are susceptible to oxidation and reduction (see U.S. Pat. Nos. 6,096,273 and 6,090,933). In this method, when DNAs are hybridized, they form a complex, together with a compound containing metal which is susceptible to oxidation and reduction, and the complex is then electrochemically detected (see Anal. Chem., Vol. 70, pp. 4670-4677, 1998; J. Am. Chem. Soc., Vol. 119, pp. 9861-9870, 1997; Analytica Chimica Acta, Vol. 286, pp. 219-224, 1994; Bioconjugate Chem., Vol. 8, pp. 906-913, 1997). However, this electrochemical method also has a disadvantage in that it requires special labeling.

Intensive studies have also been carried out to develop an analysis method without using fluorescent dyes or any other markers. Examples of the developed method include a method to measure a difference in mass before and after binding using a quartz crystal microbalance (see Anal. Chem., Vol. 70, pp. 1288-1296, 1998) and an analysis method using Matrix Assisted Laser Desorption Ionization (MALDI) mass spectrometry (Anal. Chem., Vol. 69, pp. 4540-4546, 1997, U.S. Pat. No. 6,043,031).

In another method, a difference of even one base can be analyzed using a micro-fabricated cantilever which is a mechanical sensor type for measuring the molecular binding force before and after binding of DNA probes and target molecules (see Science, Vol. 288, pp. 316-318, 2000; Proc. Natl. Acad. Sci. USA, 98, 1560, 2001).

In the biochip scanner using the above laser-induced fluorescence detection method, fluorescent signals emitted from fluorescent dyes are weak depending on detection conditions, environmental changes, or the like. Thus, to detect the fluorescent signals, it is necessary to use an expensive, highly sensitive detector such as a photomultiplier tube (PMT) and a large number of optical parts such as a dichroic filter and an emission filter, which are required for highly accurate detection. This leads to an increase in the cost of the scanner. The detection conditions are also harsh. These are obstacles to the generalization of the biochip scanner.

In the case of DNA chip detection, it is also necessary to very accurately detect deflection of cantilever beams. This requires additional equipment such as laser, thereby increasing equipment and financial losses.

DISCLOSURE OF INVENTION

Technical Problem

Therefore, the present invention has been made in view of the above problems, and it is an object of the present invention to provide a biochip detection method and apparatus using phase changes, wherein a laser beam is radiated to a biochip having immobilized probes placed thereon to cause a phase change in a phase change layer located under the biochip and the reflectance on the phase change layer according to the phase change is detected to allow reproduction or recording of bio information on the biochip.

It is another object of the invention to provide a biochip detection method using phase changes, wherein the resistance between two electrodes connected respectively to both ends of a phase change layer including a bio spot where a phase change occurs is measured so that it is possible to easily detect binding states of the biochip using phase changes in the biochip.

Technical Solution

In accordance with the present invention, the above and other objects can be accomplished by the provision of a biochip detection system that removes factors causing the increase in the price and the instability of the fluorescence detection type and adopts a phase change-based optical disc recording/reproduction technology that has a high technical completeness and reliability proved using nanobeads or nanoparticles.

Specifically, the present invention implements a method of detecting phase changes of a recording layer on a substrate of the biochip and changes in an organic dye layer based on presence or absence of nanoparticles using a DVD optical pickup mechanism and thus replaces the conventional bio information detection method based on fluorescence causing problems with a non-fluorescence detection method, thereby achieving an improvement in the performance.

Advantageous Effects

The present invention has the following advantages. A laser beam is radiated to a biochip having immobilized probes placed thereon to cause phase changes in a phase change layer located under the biochip and changes in the reflectance on the phase change layer according to the phase changes are detected to allow reproduction or recording of bio information on the biochip, thereby providing a biochip that has a simple structure and can also provide accurate detection.

According to the invention, it is also possible to record information on a biochip while detecting biochip information from the biochip. Thus, the recorded information is detected as biochip information and the information distribution property is excellent, and the information can also be stored for a long time.

In addition, signals detected according to the invention are clearer than fluorescent signals and are also highly sensitive and accurate. Thus, the system according to the invention provides easier detection and guarantees high performance when it is designed for a diagnosis scanner and also guarantees portability and ease of detection, when compared to the conventional system.

Further, high-accuracy, high-density biochips can be manufactured since nanoparticles are used.

Furthermore, after probes located above a phase change layer are removed, an erasure laser beam is radiated to the entire area of the phase change layer to bring the crystalline state of the phase change layer back to an initial state to allow the phase change layer to be reused for another biochip, so that reading and writing can be repeatedly performed on it.

According to another embodiment of the invention, phase changes in a biochip can be easily detected by measuring the resistance between two electrodes connected respectively to both ends of a phase change layer including a bio spot where a phase change occurs.

The biochip phase change detection method according to the invention simplifies the structure of the biochip phase change detection system, thereby achieving a small and inexpensive system.

MODE FOR THE INVENTION

To accomplish the above objects, the present invention provides a method for detecting biochip information using phase changes to record and reproduce biochip information, the method comprising binding target probes coated with nanoparticles (light scattering or shielding materials) to immobilized probes on an initialized biochip; radiating a write laser beam to the top of the biochip after binding the target probes to the immobilized probes so that the temperature of a radiated area where target probes are bound to immobilized probes does not reach a phase changing temperature to cause no phase change in a phase change layer and the temperature of a radiated area where target probes are not bound to immobilized probes reaches a level above the phase changing temperature to cause a phase change in the phase change layer; radiating, after causing a phase change in the phase change layer, a read laser beam to the phase change layer to determine a reflectance difference in order to detect the extent of the phase change; and converting the determined reflectance difference into an image through an A/D converter and outputting the image.

Another embodiment of the invention provides an apparatus for detecting biochip information using phase changes to record and reproduce biochip information, the apparatus comprising a biochip including a phase change layer deposited on a substrate, immobilized probes formed on a top of the phase change layer, and an array of target probes, bound to the immobilized probes, with nanoparticles (light scattering or shielding materials) being coated on tops of the target probes; laser beam scanning means for radiating a write laser beam to a top of the biochip to cause a phase change in the phase change layer and then stopping the radiation to cause a phase change in an area of the phase change layer where only immobilized probes are present so that information of binding states of the target probes of the biochip is recorded on the biochip; and reproduction means for scanning a read laser beam on the top of the biochip, detecting reflectance of the phase change layer according to phase change states of the phase change layer to read bio information recorded on the biochip, and outputting the read bio information through output means.

The invention also provides a method for detecting biochip information using phase changes, the method comprising preparing a biochip including two electrodes and a bio spot of phase change material connected between the two electrodes with immobilized probes being fixed to the bio spot; scattering target probes, including light shielding particles bound to tops of the target probes, over the biochip to bind the target probes to the immobilized probes; radiating a laser beam to the bio spot; and measuring a resistance between the two electrodes to detect whether or not a phase change has occurred.

The light shielding particles are nanoparticles which are nanoscale particles. The nanoparticles may be made of gold, silver, or copper. That is, nanoparticles capable of shielding a laser beam to cause a phase change in the bio spot are bound to the tops of the target probes.

When the target probes including the nanoparticles bound to the tops of the target probes are bound to the immobilized probes, no phase change occurs in the bio spot as the nanoparticles shield or scatter the laser beam to prevent the temperature from reaching the phase changing temperature and, when the target probes including the nanoparticles bound to the tops of the target probes are not bound to the immobilized probes, a phase change occurs in the bio spot due to the laser beam.

The resistance between the electrodes is measured to be equal to or higher than a reference resistance when a phase change has occurred in the bio spot and is measured to be less than the reference resistance when no phase change has occurred in the bio spot. The reference resistance is the resistance between the two electrodes when a phase change occurs in the bio spot. The reference resistance can be determined experimentally.

Preferred embodiments of a method and apparatus for detecting biochip information using phase changes according to the present invention, which includes the components described above, will be described in detail with reference to the accompanying drawings.

Embodiment 1

Detection Method Based on Reflectance Change

An apparatus for scanning a biochip using phase changes will be described below in detail with reference to the accompanying drawings. The following is a bio information detection principle.

First, a biochip including a phase change layer formed thereon is manufactured. The surface of the biochip is modified so that bio particles are well fixed to the biochip. Probe DNAs (immobilized probes) are then bonded to the top of the biochip. Target DNAs (target probes) labeled with nanoparticles are scattered over the phase change substrate to cause binding of the target DNAs (target probes) to the probe DNAs (immobilized probes).

The biochip is then washed to remove all target probes and immobilized probes, which have not been bound to each other, while leaving target probes and immobilized probes bound to each other on the biochip.

A write laser beam is radiated to record bio information on the phase change layer and all bio materials on it are removed. Thereafter, a read laser beam is used to read and analyze the recorded information. Here, the nanoparticles serves as important labels which shield or amplify the energy of a laser beam transferred to the phase change layer to detect presence or absence of bio materials on the phase change layer.

The phase change layer may be formed of a phase change material that is generally used as an optical recording medium. An example of the phase change material is $Ge_2Sb_2Te_5$ (GST) that is a phase change optical recording material that is widely used as a recording medium for Digital Versatile Disks (DVDs), Phase change Random Access Memory (PRAM), or the like. The GST has the characteristics of reversible phase changes between amorphous and crystalline states. Information is optically written or erased using the reversible phase change characteristics of the GST, thereby obtaining information that is required for the invention.

Reference will now be made in detail to the operation of each step of the invention according to this principle.

Figure 2:
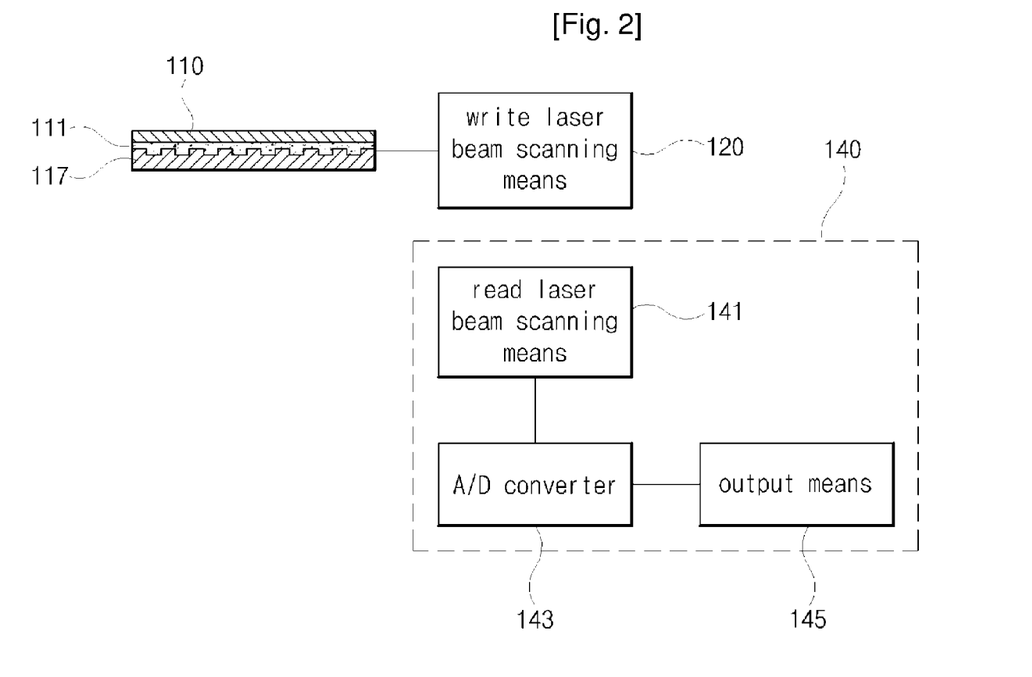
FIG. 2 illustrates a biochip scanning apparatus using phase changes according to the invention.

The apparatus for recording and reproducing biochip information according to the invention includes a biochip 110, laser beam scanning means 120, and reproduction means 140. The biochip 110 includes a phase change layer 111 deposited on a substrate 117, immobilized probes 130 formed on the top of the phase change layer 111, and an array of target probes 113, bound to the immobilized probes 130, with nanoparticles 115 being coated on the tops of the target probes 113. The laser beam scanning means 120 radiates a write laser beam to the top of the biochip 110 to cause a phase change in the phase change layer 111 and then stops the radiation to cause a phase change in an area of the phase change layer 111 where only immobilized probes 130 are present so that information of binding states of the target probes 113 of the biochip 110 is recorded on the biochip 110. The reproduction means 140 scans a read laser beam on the top of the biochip 110, detects reflectance of the phase change layer 111 according to phase change states of the phase change layer 111 to read bio information recorded on the biochip 110, and outputs the read bio information through output means 145.

The nanoparticles 115 are made of light scattering, shielding material, or the like. Specifically, gold, silver, or the like may be used as the light scattering or shielding material for the nanoparticles.

The reproduction means 140 includes laser beam scanning means 141 and an A/D converter 143. Digital information obtained at the A/D converter 143 is converted into an image and the image is then analyzed at a computer system.

With reference to the accompanying drawings, a description will now be given of how biochip information is recorded and reproduced using the biochip scanning apparatus using phase changes configured as described above.

FIGS. 1A to 1D are process diagrams of a procedure in which a biochip manufactured according to the invention is scanned according to a phase change scheme to reproduce information of the biochip.

Figure 1:
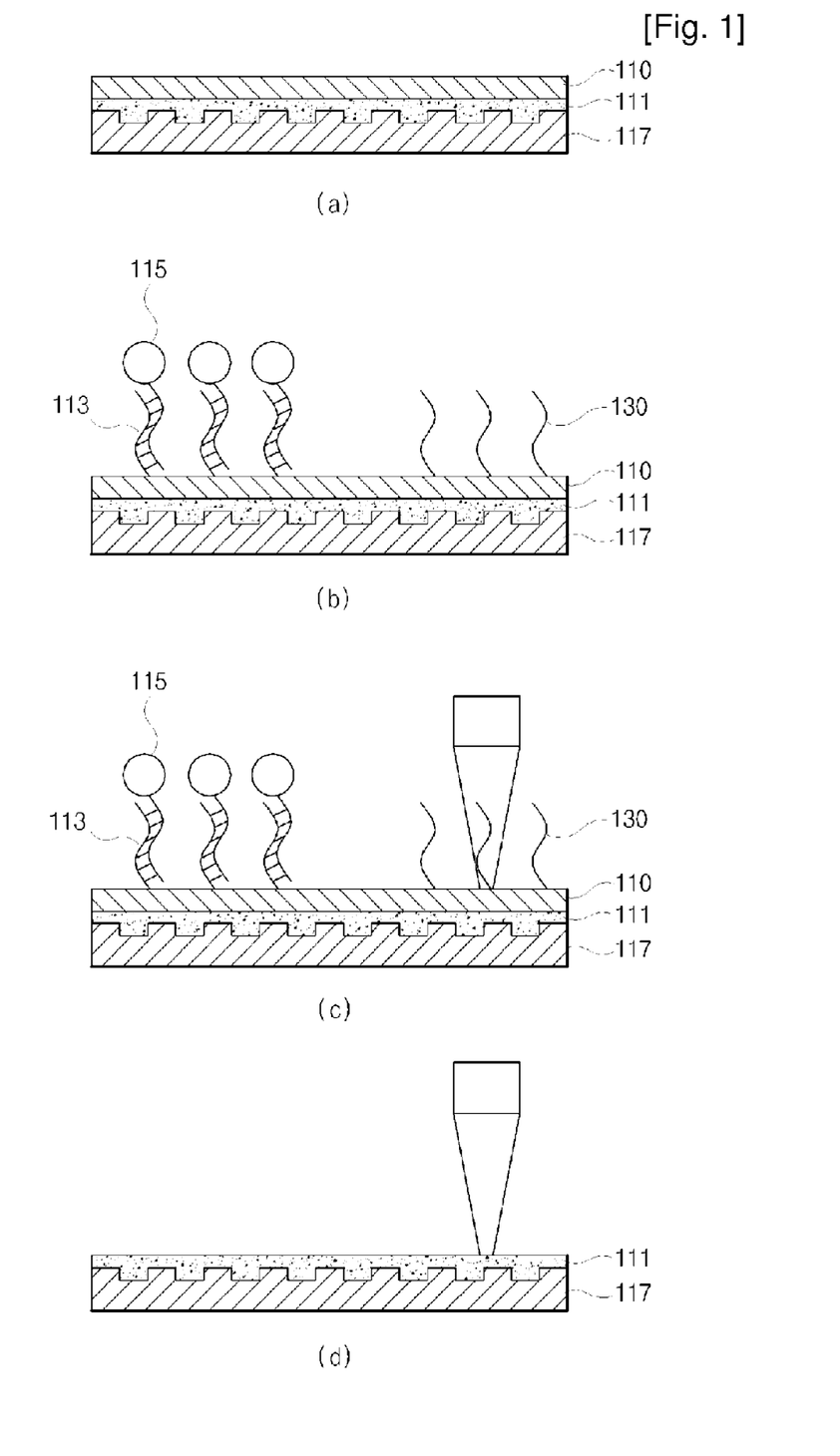
FIGS. 1A to 1D illustrate a biochip scanning method using phase changes according to the invention.

As shown in FIGS. 1A and 1B, a phase change layer 111 is provided on the top of a substrate 117 and target probes 113, coated with nanoparticles 115 which are made of light scattering or shielding material, are bound to immobilized probes 130 on an initialized biochip 110 provided on the top of the phase change layer 111.

Then, as shown in FIG. 1C, a laser beam is radiated to the top of the biochip 110 after the target probes 113 are bound to the immobilized probes 130. Accordingly, no phase change occurs in areas of the phase change layer 111 where the target probes 113 are bound to the immobilized probes 130 even though a laser beam is radiated to the areas since the light scattering or shielding material prevents the temperature of the areas from reaching a phase changing temperature at which a phase change occurs. On the other hand, a phase change occurs in areas of the phase change layer 111 where target probes 113 are not bound to immobilized probes 130 since the laser radiation raises the temperature of the areas above the phase changing temperature. The extent of the phase change varies depending on the extent to which immobilized probes are bound to target probes in this process. Based on this, it is possible to detect information of micro-bio structures formed according to the binding.

After causing a phase change in the phase change layer 111 in this manner, a read laser beam is radiated as shown in FIG. 1D to determine differences (or changes) of reflectance on the phase change layer 111. The reflectance differences are converted into an image using an A/D converter 143 and the image is then output.

Finally, a laser beam is radiated to the top of the biochip 110 to initialize the biochip 110 after reading the bio information recorded on the biochip 110. Then, the bio information detection can be repeated continuously.

The following is a summary of the biochip detection method described above. Nanoparticles are bound to target probes on a biochip having a substrate on which a phase change recording layer is patterned under bio probes and a laser optical system that causes phase changes. During DNA expression, a laser beam is radiated to the phase change recording layer to transfer information, as to whether or not bio probes have been bound to nanoparticles, to the phase change recording layer. After phase changes (crystallization) are induced in the phase change recording layer through the radiation, differences (or variations) of reflectance on the recording layer are read to detect biochip information.

Specifically, a biochip having the initialized recording layer with target probes coated with nanoparticles being bound to immobilized probes on the biochip is loaded into an analysis system. A laser beam is then radiated to the biochip. Heat generated by the radiation causes changes of phases in the recording layer or changes of crystalline structures in an organic dye layer in the recording layer in areas of the recording layer where nanoparticles are bound since the nanoparticles serve as light scattering or shielding materials. On the other hand, the laser beam is directly radiated to areas of the recording layer having immobilized probes, to which nanoparticles are not bound, thereby causing significant changes of phases in the recording layer or changes of crystalline structures in the organic dye layer in the recording layer in the areas. The reflectance on the recording layer varies depending on the extent of the phase change in the recording layer or the extent of burning of the organic dye layer. Biochip binding information is obtained through AD conversion of the reflectance variation and an image is then reproduced from the information.

Embodiment 2

Detection Method Based on Resistance Change

FIGS. 3A to 3D are process diagrams of a biochip detection method using phase changes according to an embodiment of the invention. The biochip detection method using phase changes will now be described with reference to FIGS. 3A to 3D. Each of FIGS. 3A to 3D shows two figures, the left figure illustrating a process in which no phase change occurs and the right illustrating a process in which a phase change occurs.

Figure 3:
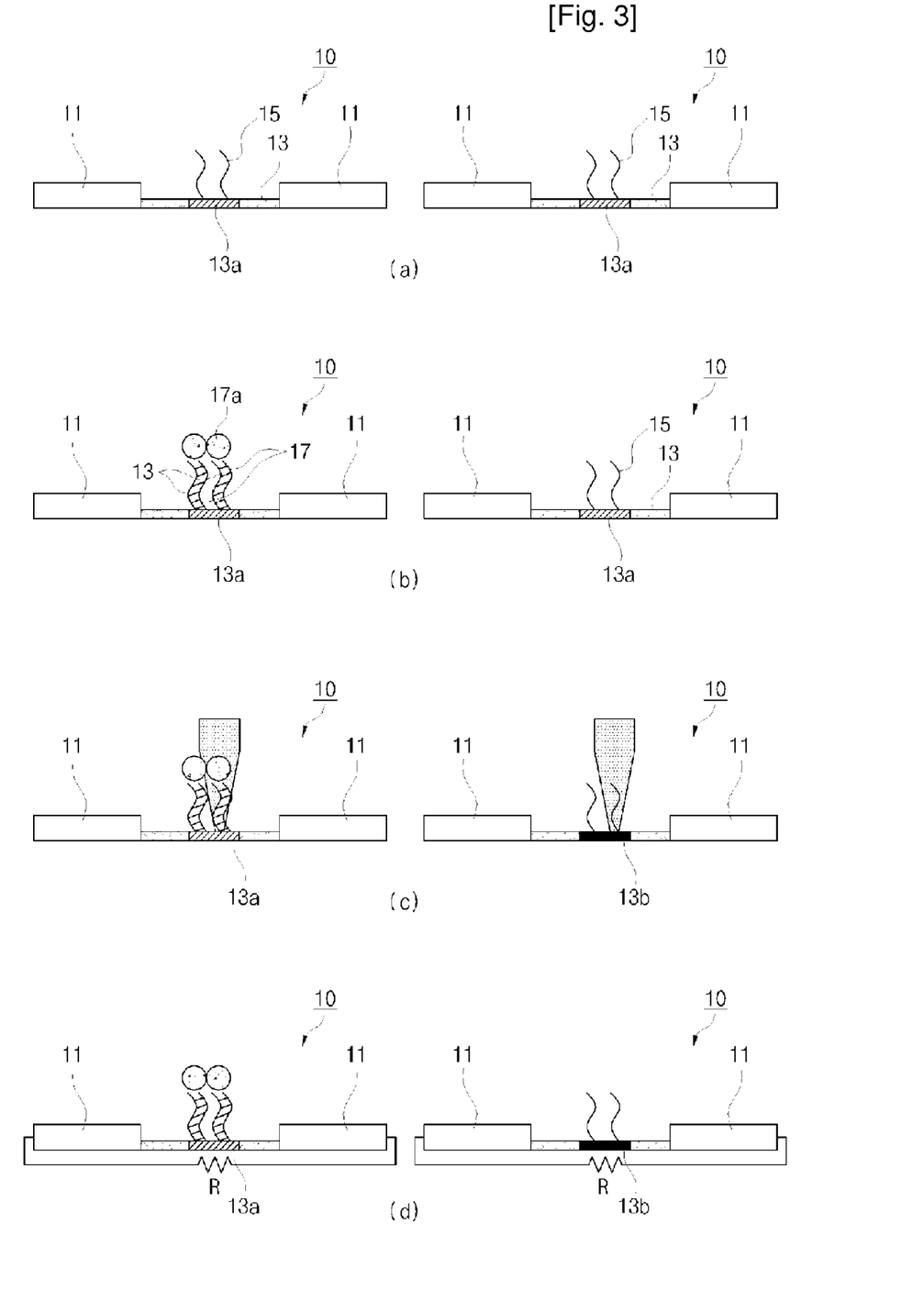
FIGS. 3A to 3D are process diagrams of a biochip detection method using phase changes according to another embodiment of the invention.

First, a biochip 10 for phase change detection is prepared as shown in FIG. 3A. In the biochip 10, a phase change material 13 is connected between two electrodes 11 as shown in FIG. 3A. A bio spot 13a where the laser beam causes a phase change is formed at a center portion of the phase change material 13 and an immobilized probe 15 is fixed to the bio spot 13a.

Target probes 17 are then scattered over the biochip 10 with the immobilized probes 15 fixed to the bio spot 13a. The target probes 17 scattered over the biochip 10 are then bound to the immobilized probes 15.

Here, it is to be noted that the target probes 17 are coated with light shielding particles which can shield or scatter light. Thus, light shielding particles are bound to the tops of the target probes 17. Light shielding or scattering particles are preferably nanoparticles which are nanoscale particles. The nanoparticles may be made of gold, silver, copper, or the like.

When the target probes 17 have been scattered over the biochip 10 in this manner, the biochip 10 will have both areas where target probes 17 are bound to immobilized probes 15 and areas where target probes 17 are not bound to immobilized probes 15. The left figure of FIG. 3B shows a biochip 10 in which target probes 17 are bound to immobilized probes and the right figure shows a biochip 10 in which target probes 17 are not bound to immobilized probes.

A laser beam is then radiated to the bio spot 13a of the biochip 10 as shown in FIG. 3C. A phase change occurs in the bio spot 13a if the radiated laser beam reaches the bio spot 13a and raises the temperature of the bio spot 13a above the phase changing temperature and no phase change occurs in the bio spot 13a if the radiated laser beam does not reach the bio spot 13a or does not raise the temperature of the bio spot 13a above the phase changing temperature.

When no obstacle is present on the bio spot 13a, the laser beam is radiated to the extent with which the temperature of the bio spot 13a is raised to the phase changing temperature causing phase changes of the bio spot 13a. The temperature of the bio spot 13a, which causes phase changes, and the radiation duration and intensity of the laser beam can be determined experimentally.

When a laser beam has been radiated to the bio spot 13a, no phase change occurs in the bio spot 13a of the biochip 10 in which target probes 17 with nanoparticles 17a connected to their tops are bound to immobilized probes 15 as shown in the left figure of FIG. 3A and a phase change occurs in the bio spot 13b of the biochip 10 in which target probes 17 with nanoparticles 17a connected to their tops are not bound to immobilized probes 15 as shown in the right figure of FIG. 3A.

The reason why no phase change occurs in the bio spot 13a is that the nanoparticles 17a coated on the target probes 17 bound to the immobilized probes 15 shield the laser beam as shown in the left figure of FIG. 3C. That is, the temperature of the bio spot 13a is not raised above the phase changing temperature since the nanoparticles shield the laser beam so that the laser beam is not or is partially radiated to the bio spot 13a.

On the other hand, the reason why a phase change occurs in the bio spot 13b is that target probes 17 are not bound to immobilized probes 15 so that the laser beam is not shielded as shown in the right figure of FIG. 3C. That is, the temperature of the bio spot 13b is raised above the phase changing temperature since the laser beam is not shielded by any nanoparticle so that it is directly radiated to the bio spot 13b. The radiation duration and intensity of the laser beam are controlled to allow the temperature of the bio spot to be raised above the phase changing temperature.

After the laser beam is radiated in this manner, a resistance R between the two electrodes 11 is measured to detect whether or not a phase change has occurred. The resistance between the electrodes 11 is measured to be equal to or higher than a reference resistance when a phase change has occurred in the bio spot 13b as shown in the right figure of FIG. 3D and is measured to be less than the reference resistance when no phase change has occurred in the bio spot 13a as shown in the left figure of FIG. 3D.

The reference resistance can be set to a level at which a phase change occurs in the bio spot. The reference resistance can be previously determined experimentally. Whether or not a phase change has occurred can be determined by comparing the measured resistance between the electrodes 11 with the reference resistance.

It can be determined that a phase change has occurred in the bio spot if the measured resistance is equal to or higher than the reference resistance and that no phase change has occurred in the bio spot if the measured resistance is less than the reference resistance.

In a more specific embodiment of the laser beam radiation to detect whether or not a phase change has occurred as described above, a laser illumination device of the detector can be used to detect hybridization resulting from complementary binding of sample and probe DNAs on a phase change biochip. To determine whether or not target DNAs (target probes) labeled with Au nanoparticles have been hybridized with probe DNAs (immobilized probes) fixed on a phase change material connecting electrode structures in the biochip and also to determine the strength of the hybridization, a laser beam is radiated to a bio spot (i.e., a DNA spot) on the biochip to cause phase changes (crystallization) in the small area for tens of nanoseconds.

Optimal detection conditions required for phase changes can be searched for while controlling the recording power, recording time, and waveform (or wavelength) of the laser beam radiated to the biochip and the thin film structure of a chip, which is a sample having upper and lower electrode patterns, is constructed by sequentially depositing a $Ge_2Sb_2Te_5$ layer, a protective layer, and a combination of probe DNAs and DNAs labeled with Au nanoparticles on a substrate.

Particularly, based on whether or not crystallization has occurred in a phase change layer included in the chip, it is possible to determine whether or not a phase change (crystallization) has occurred in the probe spot due to the hybridization with nanoparticle-labeled DNAs according to the invention. Whether or not crystallization has occurred can be determined by detecting changes in the reflectance or resistance of the phase change layer. The extent of the crystallization of the spot according to the strength of the hybridization binding to nanoparticle-labeled DNAs can be determined according to the proportionality of the extent of crystallization with the strength of hybridization.

Figure 4:
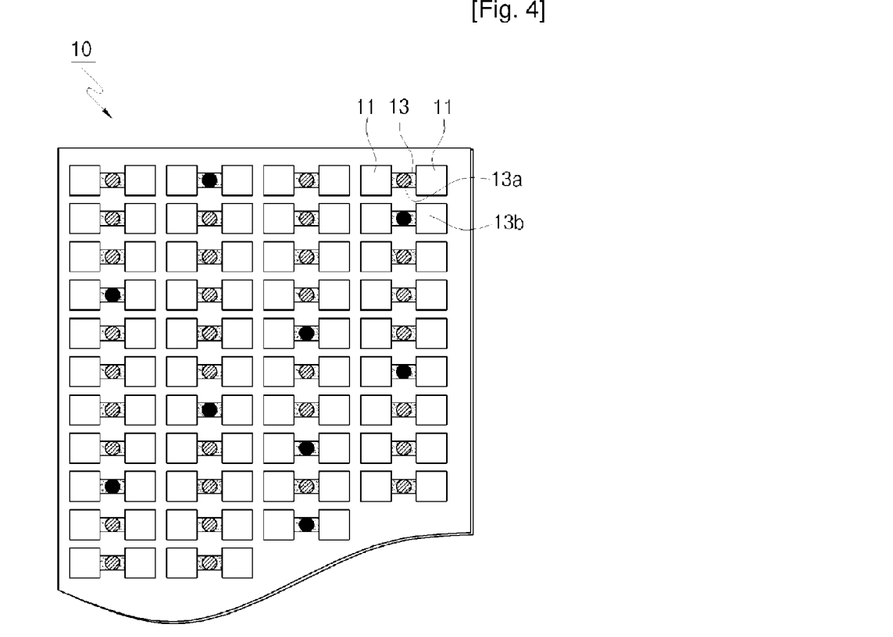
FIG. 4 is a plan view showing a biochip pattern where phase changes have occurred according to another embodiment of the invention.

FIG. 4 shows the pattern of a biochip having both bio spots where a phase change has occurred and bio spots where no phase change has occurred as described above. In FIG. 4, no phase change has occurred in each shaded bio spot 13a and a phase change has occurred in each black bio spot 13b. Whether or not a phase change has occurred in each bio spot can be collectively determined by measuring the resistance between each pair of electrodes at the same time.

Figure 5:
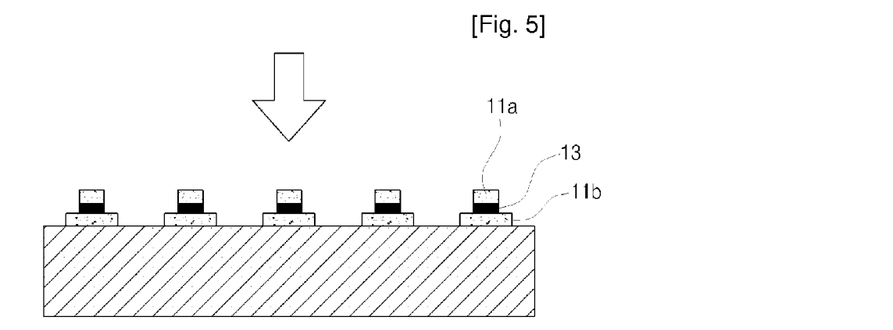
FIGS. 5 to 7 schematically illustrate a phase change layer and electrodes according to an embodiment of the invention.
Figure 6:
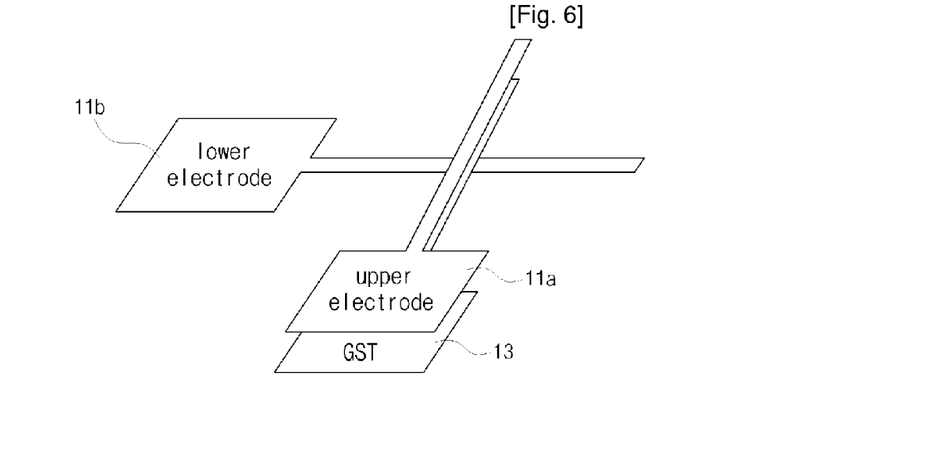
Figure 7:
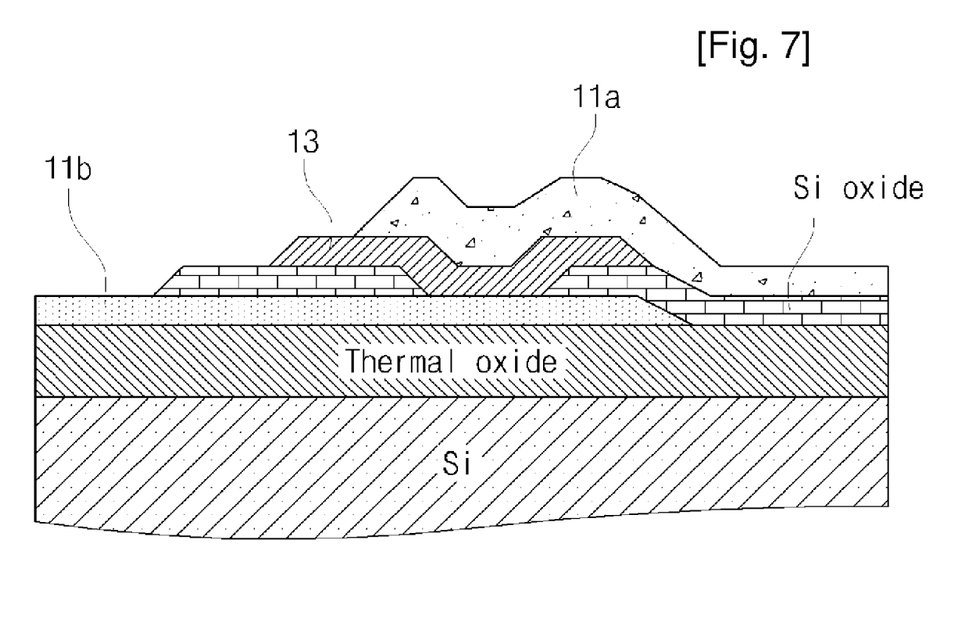

FIGS. 5 to 7 illustrate an embodiment of a biochip structure in which upper and lower electrodes and the phase change layer described above are arranged.

FIG. 5 shows a Phase change Random Access Memory (PRAM) structure with an arrangement of a phase change GST layer and electrodes. This structure is formed by sequentially stacking a lower electrode 11b, a GST layer 13, and an upper electrode 11a on the top of a substrate. The GST layer 13 and the electrodes 11a and 11b are generally arranged as shown in FIG. 6. FIG. 7 shows a sectional structure in which a thermal oxide layer is formed on a Si layer and a lower electrode 11b, a phase change layer 13 and an upper electrode 11b are stacked on the top of the thermal oxide layer.

Although the specific embodiments of the present invention have been described for illustrative purposes, those skilled in the art will appreciate that various modifications are possible without departing from the scope and spirit of the invention. The scope of the invention should be determined by the appended claims and their equivalents, not by the embodiments described above.

INDUSTRIAL APPLICABILITY

A biochip detection method and apparatus according to the present invention provides a new semiconductor-type biochip for disease diagnosis and a simple resistance detection analysis device (having an optical disc drive structure such as DVD or a tester structure equipped with a DC battery) which requires no expensive, large-size fluorescent scanner analysis equipment. This can reduce the size of the equipment for detecting genes, proteins, harmful food germs, GMOs, and bacteria and can also increase the portability of the equipment and promote the spread of relevant technologies, thereby having significant effects on the field of use of the equipment.

According to the invention, both an electrode structure of a semiconductor chip, which is smaller than the conventional DNA/protein chip with fluorescent markers, and a method of detecting changes in the resistance of a phase change material are used so that the entire size of the detection device is reduced and the portability is also increased. Low-cost mass production is also possible since a mass-producible PRAM type semiconductor chip is used. Further, a macromolecular plastic (polycarbonate) substrate is used in place of a silicon substrate, thereby allowing mass production of lower-priced biochips.

The invention claimed is:

1. An apparatus for detecting biochip information using phase changes to record and reproduce biochip information, the apparatus comprising:
   a biochip including a phase change layer deposited on a substrate, immobilized probes formed on a top of the phase change layer, and an array of target probes, bound to the immobilized probes, with nanoparticles being coated on tops of the target probes;
   laser beam scanning means for radiating a write laser beam to a top of the biochip to cause a phase change in the phase change layer and then stopping the radiation to cause a phase change in an area of the phase change layer where only immobilized probes are present so that information of binding states of the target probes of the biochip is recorded on the biochip; and
   reproduction means for scanning a read laser beam on the top of the biochip, detecting reflectance of the phase change layer according to phase change states of the phase change layer to read bio information recorded on the biochip, and outputting the read bio information through output means.

2. The apparatus according to claim 1, wherein the nanoparticles are made of light scattering or shielding material.

3. The apparatus according to claim 2, wherein the reproduction means includes laser beam scanning means and an A/D converter.

4. A method for detecting biochip information using phase changes to record and reproduce biochip information, the method comprising:
   binding target probes coated with nanoparticles to immobilized probes on an initialized biochip;
   radiating a write laser beam to a top of the biochip after binding the target probes to the immobilized probes so that the temperature of a radiated area where target probes are bound to immobilized probes does not reach a phase changing temperature to cause no phase change in a phase change layer and the temperature of a radiated area where target probes are not bound to immobilized probes reaches a level above the phase changing temperature to cause the phase change in a phase change layer;
   radiating a read laser beam to the phase change layer to determine a reflectance difference after causing a phase change in the phase change layer; and
   outputting the determined reflectance difference to an A/D converter to obtain a digital image.

5. The method according to claim 4, wherein the nanoparticles are made of light scattering or shielding material.

6. The method according to claim 5, further comprising radiating a laser beam to the top of the biochip after reading bio information recorded on the biochip to initialize the biochip.

7. A method for detecting biochip information using phase changes, the method comprising:
   preparing a biochip including two electrodes and a bio spot of phase change material connected between the two electrodes with immobilized probes being fixed to the bio spot;
   scattering target probes, including light shielding particles bound to tops of the target probes for light shielding or scattering, over the biochip to bind the target probes to the immobilized probes;
   radiating a laser beam to the bio spot; and
   measuring a resistance between the two electrodes to detect whether or not a phase change has occurred.

8. The method according to claim 7, wherein the light shielding particles are nanoparticles which are nanoscale particles.

9. The method according to claim 8, wherein the nanoparticles are made of one of gold, silver, and copper.

10. The method according to claim 8, wherein no phase change occurs in the bio spot as the nanoparticles shield the laser beam when the target probes including the nanoparticles bound to the tops of the target probes are bound to the immobilized probes and a phase change occurs in the bio spot due to the laser beam when the target probes including the nanoparticles bound to the tops of the target probes are not bound to the immobilized probes.

11. The method according to claim 10, wherein the resistance between the electrodes is measured to be equal to or higher than a reference resistance when a phase change has occurred in the bio spot and is measured to be less than the reference resistance when no phase change has occurred in the bio spot and binding states of the biochip are detected from the resistance.

* * * * *